(12) United States Patent
Bowen et al.

(10) Patent No.: US 11,904,089 B2
(45) Date of Patent: Feb. 20, 2024

(54) DEVICES FOR VAPORIZATION OF A SUBSTANCE

(71) Applicant: JUUL Labs, Inc., San Francisco, CA (US)

(72) Inventors: Adam Bowen, San Mateo, CA (US); Krista Hunter, San Francisco, CA (US); James Monsees, San Francisco, CA (US); Patrick A. Myall, San Francisco, CA (US)

(73) Assignee: JUUL Labs, Inc., Washington, DC (US)

( * ) Notice: Subject to any disclaimer, the term of this patent is extended or adjusted under 35 U.S.C. 154(b) by 901 days.

(21) Appl. No.: 16/372,354

(22) Filed: Apr. 1, 2019

(65) Prior Publication Data

US 2019/0223510 A1    Jul. 25, 2019

Related U.S. Application Data

(63) Continuation of application No. 15/165,954, filed on May 26, 2016, now Pat. No. 10,244,793, which is a
(Continued)

(51) Int. Cl.
*A61M 15/06* (2006.01)
*A61M 15/00* (2006.01)
(Continued)

(52) U.S. Cl.
CPC ............... *A61M 15/06* (2013.01); *A24F 1/32* (2013.01); *A24F 7/02* (2013.01); *A24F 13/04* (2013.01);
(Continued)

(58) Field of Classification Search
None
See application file for complete search history.

(56) References Cited

U.S. PATENT DOCUMENTS

| 720,007 A | 2/1903 | Dexter |
| 1,165,000 A | 12/1915 | Dula |

(Continued)

FOREIGN PATENT DOCUMENTS

| CA | 1329098 C | 5/1994 |
| CA | 2641869 A1 | 5/2010 |

(Continued)

OTHER PUBLICATIONS

U.S. Appl. No. 11/485,168, filed Jun. 11, 2006, U.S. Pat. No. 9,675,109.
(Continued)

*Primary Examiner* — Phu H Nguyen
(74) *Attorney, Agent, or Firm* — Mintz, Levin, Cohn, Ferris, Glovsky and Popeo, P.C.

(57) ABSTRACT

Devices for generating and releasing vapor. In particular, described herein are portable devices for generating a low-temperature inhalable vapor having an elongated tubular body containing a vaporization chamber and a battery-powered heater, a removable mouthpiece covering the vaporization chamber, a display configured to indicate the temperature of the vaporization chamber; a microcontroller configured to regulate the temperature of the vaporization chamber, and a control to select from among a variety of temperature settings.

14 Claims, 6 Drawing Sheets

Related U.S. Application Data continuation-in-part of application No. 13/837,438, filed on Mar. 15, 2013, now abandoned, which is a continuation-in-part of application No. 13/587,416, filed on Aug. 16, 2012, now Pat. No. 9,408,416.

(60) Provisional application No. 61/524,308, filed on Aug. 16, 2011.

(51) Int. Cl.

| | |
|---|---|
| A61M 11/04 | (2006.01) |
| A61M 11/00 | (2006.01) |
| A24F 40/42 | (2020.01) |
| A24F 40/46 | (2020.01) |
| A24F 40/51 | (2020.01) |
| A24F 40/53 | (2020.01) |
| A24F 40/60 | (2020.01) |
| A24F 40/90 | (2020.01) |
| G08B 5/36 | (2006.01) |
| H05B 1/02 | (2006.01) |
| G05B 11/36 | (2006.01) |
| A24F 1/32 | (2006.01) |
| A24F 7/02 | (2006.01) |
| A24F 13/04 | (2006.01) |
| B01B 1/00 | (2006.01) |
| F21V 33/00 | (2006.01) |
| G05D 23/19 | (2006.01) |
| G06F 3/147 | (2006.01) |
| H05B 3/14 | (2006.01) |
| H05B 3/34 | (2006.01) |
| A61M 16/00 | (2006.01) |
| A24F 40/10 | (2020.01) |
| G06F 3/02 | (2006.01) |
| F21Y 115/10 | (2016.01) |

(52) U.S. Cl.
CPC ............ *A24F 40/42* (2020.01); *A24F 40/46* (2020.01); *A24F 40/51* (2020.01); *A24F 40/53* (2020.01); *A24F 40/60* (2020.01); *A24F 40/90* (2020.01); *A61M 11/00* (2013.01); *A61M 11/041* (2013.01); *A61M 11/042* (2014.02); *A61M 11/048* (2014.02); *A61M 15/0023* (2014.02); *A61M 15/0025* (2014.02); *A61M 15/0026* (2014.02); *A61M 15/0028* (2013.01); *B01B 1/005* (2013.01); *F21V 33/0004* (2013.01); *G05B 11/36* (2013.01); *G05D 23/1917* (2013.01); *G06F 3/147* (2013.01); *G08B 5/36* (2013.01); *H05B 1/0244* (2013.01); *H05B 3/146* (2013.01); *H05B 3/34* (2013.01); *A24F 40/10* (2020.01); *A61M 11/007* (2014.02); *A61M 15/00* (2013.01); *A61M 2016/0024* (2013.01); *A61M 2205/0266* (2013.01); *A61M 2205/332* (2013.01); *A61M 2205/3368* (2013.01); *A61M 2205/581* (2013.01); *A61M 2205/582* (2013.01); *A61M 2205/8206* (2013.01); *A61M 2205/8237* (2013.01); *A61M 2209/084* (2013.01); *F04C 2270/041* (2013.01); *F21Y 2115/10* (2016.08); *G06F 3/02* (2013.01); *H05B 2203/021* (2013.01)

(56) References Cited

U.S. PATENT DOCUMENTS

| | | |
|---|---|---|
| 2,104,266 A | 1/1938 | McCormick |
| 2,158,928 A | 5/1939 | Deich |
| 2,159,698 A | 5/1939 | Harris et al. |
| 2,177,636 A | 10/1939 | Coffelt et al. |
| 2,195,260 A | 3/1940 | Rasener |
| 2,830,597 A | 4/1958 | Kummli |
| 2,860,638 A | 11/1958 | Bartolomeo |
| 2,935,987 A | 5/1960 | Ackerbauer |
| 3,200,819 A | 8/1965 | Gilbert |
| 3,292,634 A | 12/1966 | Beucler |
| 3,443,827 A | 5/1969 | Acker et al. |
| 3,456,645 A | 7/1969 | Brock |
| 3,565,071 A | 2/1971 | Cobb et al. |
| 3,610,880 A | 10/1971 | Kreiberg |
| 3,675,661 A | 7/1972 | Weaver |
| 3,707,017 A | 12/1972 | Paquette |
| 3,792,704 A | 2/1974 | Parker |
| 3,810,258 A | 5/1974 | Mathauser |
| 3,815,597 A | 6/1974 | Goettelman |
| 4,020,853 A | 5/1977 | Nuttall |
| 4,036,224 A | 7/1977 | Choporis et al. |
| 4,049,005 A | 9/1977 | Hernandez et al. |
| 4,066,088 A | 1/1978 | Ensor |
| 4,175,571 A | 11/1979 | Swanson |
| 4,215,708 A | 8/1980 | Bron |
| 4,219,032 A | 8/1980 | Tabatznik et al. |
| 4,269,203 A | 5/1981 | Corbett |
| 4,303,083 A | 12/1981 | Burruss, Jr. |
| 4,506,683 A | 3/1985 | Cantrell et al. |
| 4,534,367 A | 8/1985 | Newsome |
| 4,648,393 A | 3/1987 | Landis et al. |
| 4,708,151 A | 11/1987 | Shelar |
| 4,793,365 A | 12/1988 | Sensabaugh, Jr. et al. |
| 4,819,665 A | 4/1989 | Roberts et al. |
| 4,848,374 A | 7/1989 | Chard et al. |
| 4,944,317 A | 7/1990 | Thal |
| 4,947,874 A | 8/1990 | Brooks et al. |
| 4,947,875 A | 8/1990 | Brooks et al. |
| 4,967,774 A | 11/1990 | White |
| 4,987,908 A | 1/1991 | Sprinkel et al. |
| 5,020,548 A | 6/1991 | Farrier et al. |
| 5,027,836 A | 7/1991 | Shannon et al. |
| 5,050,621 A | 9/1991 | Creighton et al. |
| 5,060,671 A | 10/1991 | Counts et al. |
| 5,105,838 A | 4/1992 | White et al. |
| 5,144,962 A * | 9/1992 | Counts .................. A24D 1/20 131/194 |
| 5,152,456 A | 10/1992 | Ross et al. |
| 5,154,192 A | 10/1992 | Sprinkel et al. |
| 5,183,062 A | 2/1993 | Clearman et al. |
| 5,203,355 A | 4/1993 | Clearman et al. |
| 5,249,586 A | 10/1993 | Morgan et al. |
| 5,261,424 A | 11/1993 | Sprinkel, Jr. |
| 5,269,327 A | 12/1993 | Counts et al. |
| 5,296,685 A | 3/1994 | Burstein et al. |
| 5,303,720 A | 4/1994 | Banerjee et al. |
| 5,456,269 A | 10/1995 | Kollasch |
| 5,479,948 A | 1/1996 | Counts et al. |
| 5,497,791 A | 3/1996 | Bowen et al. |
| 5,505,214 A | 4/1996 | Collins et al. |
| 5,529,078 A | 6/1996 | Rehder et al. |
| 5,551,416 A | 9/1996 | Stimpson et al. |
| 5,564,442 A | 10/1996 | MacDonald et al. |
| 5,573,692 A | 11/1996 | Das et al. |
| 5,649,552 A | 7/1997 | Cho et al. |
| 5,649,554 A | 7/1997 | Sprinkel et al. |
| 5,666,977 A | 9/1997 | Higgins et al. |
| 5,730,118 A | 3/1998 | Hermanson |
| 5,819,756 A | 10/1998 | Mielordt |
| 5,843,014 A | 12/1998 | Lattin et al. |
| 5,894,841 A | 4/1999 | Voges |
| 5,931,828 A | 8/1999 | Durkee |
| 5,954,979 A | 9/1999 | Counts et al. |
| 6,040,560 A | 3/2000 | Fleischhauer et al. |
| 6,089,857 A | 7/2000 | Matsuura et al. |
| 6,095,153 A | 8/2000 | Kessler et al. |
| 6,155,268 A | 12/2000 | Takeuchi |
| 6,164,287 A | 12/2000 | White |
| 6,196,232 B1 | 3/2001 | Chkadua |
| 6,272,933 B1 | 8/2001 | Gradon et al. |
| 6,324,261 B1 | 11/2001 | Merte |

(56) References Cited

U.S. PATENT DOCUMENTS

| | | |
|---|---|---|
| 6,407,371 B1 | 6/2002 | Toya et al. |
| 6,513,524 B1 | 2/2003 | Storz |
| 6,532,965 B1 | 3/2003 | Abhulimen et al. |
| 6,603,924 B2 | 8/2003 | Brown et al. |
| 6,612,404 B2 | 9/2003 | Sweet et al. |
| 6,772,756 B2 | 8/2004 | Shayan |
| 6,810,883 B2 | 11/2004 | Felter et al. |
| 6,827,573 B2 | 12/2004 | St. Charles et al. |
| 6,889,687 B1 | 5/2005 | Olsson |
| 7,019,491 B2 | 3/2006 | Bozzone et al. |
| 7,434,584 B2 | 10/2008 | Steinberg |
| 7,530,352 B2 | 5/2009 | Childers et al. |
| 7,801,573 B2 | 9/2010 | Yazdi et al. |
| 7,832,410 B2 | 11/2010 | Hon |
| 8,251,060 B2 | 8/2012 | White et al. |
| 8,371,310 B2 | 2/2013 | Brenneise |
| 8,387,612 B2 | 3/2013 | Damani et al. |
| 8,714,150 B2 | 5/2014 | Alelov |
| 9,408,416 B2 | 8/2016 | James et al. |
| 10,834,964 B2 | 11/2020 | James et al. |
| 2001/0015209 A1 | 8/2001 | Zielke |
| 2002/0029779 A1 | 3/2002 | Schmidt et al. |
| 2002/0078951 A1 | 6/2002 | Nichols et al. |
| 2003/0005926 A1 | 1/2003 | Jones et al. |
| 2003/0033055 A1 | 2/2003 | McRae et al. |
| 2003/0125075 A1 | 7/2003 | Klovborg |
| 2003/0150451 A1 | 8/2003 | Shayan |
| 2004/0031495 A1 | 2/2004 | Steinberg |
| 2004/0089314 A1 | 5/2004 | Felter et al. |
| 2004/0090539 A1 | 5/2004 | Kim et al. |
| 2004/0173229 A1 | 9/2004 | Crooks et al. |
| 2004/0187879 A1 | 9/2004 | Iordan |
| 2004/0221857 A1 | 11/2004 | Dominguez |
| 2004/0237974 A1 | 12/2004 | Min |
| 2005/0016550 A1 | 1/2005 | Katase |
| 2005/0022806 A1 | 2/2005 | Beaumont et al. |
| 2005/0067503 A1 | 3/2005 | Katase |
| 2005/0134215 A1 | 6/2005 | Bozzone et al. |
| 2005/0150488 A1 | 7/2005 | Dave |
| 2005/0251289 A1* | 11/2005 | Bonney .................. A61P 11/08 705/3 |
| 2005/0268911 A1 | 12/2005 | Cross et al. |
| 2006/0102175 A1 | 5/2006 | Nelson |
| 2007/0006889 A1 | 1/2007 | Kobal et al. |
| 2007/0045288 A1 | 3/2007 | Nelson |
| 2007/0062523 A1 | 3/2007 | Sexton et al. |
| 2007/0125372 A1 | 6/2007 | Chen |
| 2007/0125765 A1 | 6/2007 | Nelson |
| 2007/0267031 A1 | 11/2007 | Hon |
| 2007/0283972 A1 | 12/2007 | Monsees et al. |
| 2008/0000763 A1 | 1/2008 | Cove |
| 2008/0023003 A1 | 1/2008 | Rosenthal |
| 2008/0065176 A1 | 3/2008 | Zhang et al. |
| 2008/0092912 A1 | 4/2008 | Robinson et al. |
| 2008/0121244 A1 | 5/2008 | Bryman et al. |
| 2008/0150482 A1 | 6/2008 | Yazdi et al. |
| 2008/0214103 A1 | 9/2008 | Nelson et al. |
| 2008/0216828 A1 | 9/2008 | Wensley et al. |
| 2008/0233053 A1 | 9/2008 | Gross et al. |
| 2008/0257367 A1 | 10/2008 | Paterno et al. |
| 2009/0056708 A1 | 3/2009 | Stenzler et al. |
| 2009/0071469 A1 | 3/2009 | Abrams |
| 2009/0095287 A1 | 4/2009 | Emarlou |
| 2009/0110379 A1* | 4/2009 | McGhin ............ A61M 16/1095 392/485 |
| 2009/0111287 A1 | 4/2009 | Lindberg et al. |
| 2009/0126745 A1 | 5/2009 | Hon |
| 2009/0133691 A1 | 5/2009 | Yamada et al. |
| 2009/0141196 A1 | 6/2009 | Basner et al. |
| 2009/0151717 A1 | 6/2009 | Bowen et al. |
| 2009/0177253 A1 | 7/2009 | Darm et al. |
| 2009/0178672 A1 | 7/2009 | Mullinger et al. |
| 2009/0192443 A1 | 7/2009 | Collins, Jr. |
| 2009/0230117 A1 | 9/2009 | Fernando et al. |
| 2009/0239581 A1 | 9/2009 | Lee |
| 2009/0272379 A1 | 11/2009 | Thorens et al. |
| 2009/0283103 A1 | 11/2009 | Nielsen et al. |
| 2009/0288668 A1 | 11/2009 | Inagaki |
| 2009/0293892 A1 | 12/2009 | Williams et al. |
| 2009/0301363 A1 | 12/2009 | Damani et al. |
| 2009/0302019 A1 | 12/2009 | Selenski et al. |
| 2009/0308387 A1 | 12/2009 | Andersen et al. |
| 2010/0006092 A1 | 1/2010 | Hale et al. |
| 2010/0156193 A1 | 6/2010 | Rhodes et al. |
| 2010/0163063 A1 | 7/2010 | Fernando et al. |
| 2010/0242956 A1 | 9/2010 | Yamada et al. |
| 2010/0242974 A1* | 9/2010 | Pan ....................... A61M 15/06 131/273 |
| 2010/0313901 A1 | 12/2010 | Fernando et al. |
| 2011/0030706 A1 | 2/2011 | Gibson et al. |
| 2011/0036346 A1 | 2/2011 | Cohen et al. |
| 2011/0040235 A1 | 2/2011 | Castel |
| 2011/0041861 A1 | 2/2011 | Sebastian et al. |
| 2011/0094523 A1 | 4/2011 | Thorens et al. |
| 2011/0097060 A1* | 4/2011 | Michael Buzzetti ........................ A61M 11/042 392/394 |
| 2011/0105096 A1 | 5/2011 | Dods et al. |
| 2011/0108023 A1 | 5/2011 | McKinney et al. |
| 2011/0120482 A1 | 5/2011 | Brenneise |
| 2011/0126831 A1 | 6/2011 | Pernia |
| 2011/0132992 A1 | 6/2011 | Hoppe |
| 2011/0226236 A1 | 9/2011 | Buchberger |
| 2011/0226266 A1 | 9/2011 | Tao |
| 2011/0236002 A1 | 9/2011 | Oglesby et al. |
| 2011/0240047 A1 | 10/2011 | Adamic |
| 2011/0253139 A1 | 10/2011 | Guthrie et al. |
| 2011/0265788 A1 | 11/2011 | Wu |
| 2012/0086391 A1 | 4/2012 | Smith |
| 2012/0097660 A1 | 4/2012 | Bao |
| 2012/0199572 A1 | 8/2012 | Shen et al. |
| 2012/0255546 A1 | 10/2012 | Goetz et al. |
| 2012/0325227 A1 | 12/2012 | Robinson et al. |
| 2013/0042864 A1 | 2/2013 | Adler et al. |
| 2013/0042865 A1 | 2/2013 | Monsees et al. |
| 2013/0099025 A1 | 4/2013 | McDonnell |
| 2013/0099757 A1 | 4/2013 | Ham |
| 2013/0255702 A1 | 10/2013 | Griffith, Jr. et al. |
| 2013/0298905 A1 | 11/2013 | Levin et al. |
| 2013/0312742 A1 | 11/2013 | Monsees et al. |
| 2015/0101606 A1 | 4/2015 | White |
| 2015/0305409 A1 | 10/2015 | Verleur et al. |
| 2016/0007654 A1 | 1/2016 | Zhu |
| 2016/0331034 A1 | 11/2016 | Cameron |
| 2019/0223510 A1 | 7/2019 | Bowen et al. |

FOREIGN PATENT DOCUMENTS

| | | |
|---|---|---|
| CH | 508360 A | 6/1971 |
| CN | 86204805 U | 6/1987 |
| CN | 87101954 A | 10/1987 |
| CN | 86102917 A | 11/1987 |
| CN | 87202001 U | 12/1987 |
| CN | 88100383 A | 3/1988 |
| CN | 1043077 A | 6/1990 |
| CN | 1044391 A | 8/1990 |
| CN | 2103908 U | 5/1992 |
| CN | 2121128 U | 11/1992 |
| CN | 1087497 A | 6/1994 |
| CN | 1191696 A | 9/1998 |
| CN | 1195270 A | 10/1998 |
| CN | 2293957 Y | 10/1998 |
| CN | 1216903 A | 5/1999 |
| CN | 1233158 A | 10/1999 |
| CN | 1260688 A | 7/2000 |
| CN | 1284464 A | 2/2001 |
| CN | 1333657 A | 1/2002 |
| CN | 1397237 A | 2/2003 |
| CN | 1541577 A | 11/2004 |
| CN | 1575135 A | 2/2005 |
| CN | 1575136 A | 2/2005 |
| CN | 1575673 A | 2/2005 |
| CN | 1630476 A | 6/2005 |
| CN | 1633247 A | 6/2005 |

(56) References Cited

FOREIGN PATENT DOCUMENTS

| | | |
|---|---|---|
| CN | 100566769 C | 12/2009 |
| CN | 100593982 C | 3/2010 |
| CN | 201630238 U | 11/2010 |
| CN | 101932352 A | 12/2010 |
| CN | 101557728 B | 4/2011 |
| CN | 103929985 A | 7/2014 |
| DE | 4200639 A1 | 7/1992 |
| DE | 19854005 A1 | 5/2000 |
| DE | 19854009 A | 5/2000 |
| DE | 19854009 A1 | 5/2000 |
| DE | 19854012 A1 | 5/2000 |
| EP | 0129985 A1 | 1/1985 |
| EP | 0241698 A1 | 10/1987 |
| EP | 0295122 A2 | 12/1988 |
| EP | 0311581 A1 | 4/1989 |
| EP | 0336457 A2 | 10/1989 |
| EP | 354661 A2 | 2/1990 |
| EP | 0409566 A1 | 1/1991 |
| EP | 0430559 A2 | 6/1991 |
| EP | 0858744 A1 | 8/1998 |
| EP | 0893071 A | 1/1999 |
| EP | 0845220 B1 | 9/2003 |
| FR | 409989 A | 5/1910 |
| FR | 2654002 A1 | 5/1991 |
| GB | 873410 A | 7/1961 |
| GB | 1025630 A | 4/1966 |
| GB | 1185887 A | 3/1970 |
| GB | 1213318 A | 11/1970 |
| GB | 2115676 A | 9/1983 |
| JP | S59-178456 A | 10/1984 |
| JP | S61-092295 U | 6/1986 |
| JP | 62-224277 | 10/1987 |
| JP | S62-278975 A | 12/1987 |
| JP | H02-124082 A | 5/1990 |
| JP | H03-049671 A | 3/1991 |
| JP | H05-115272 A | 5/1993 |
| JP | H-08942 U | 1/1996 |
| JP | 08-000942 | 6/1996 |
| JP | H08-942 U | 6/1996 |
| JP | 2006/3239440 | 11/1996 |
| JP | H11-178563 A | 7/1999 |
| JP | 2000236865 A | 9/2000 |
| JP | 2005034021 A | 2/2005 |
| JP | 2005-058421 A | 3/2005 |
| JP | 2005506080 A | 3/2005 |
| JP | 2009148233 A | 7/2009 |
| JP | 2010/088653 A | 4/2010 |
| JP | 2011/066476 A | 3/2011 |
| KR | 10-0178387 | 11/1998 |
| KR | 1019920017583 | 2/1999 |
| KR | 10-1999-0037661 A | 5/1999 |
| KR | 20-1999-0015691 A | 5/1999 |
| KR | 100193885 B1 | 6/1999 |
| KR | 100265817 B1 | 9/2000 |
| KR | 20070112908 A | 11/2007 |
| KR | 2009/0010954 A | 1/2009 |
| KR | 2009/0023742 A | 3/2009 |
| KR | 100971178 B1 | 7/2010 |
| KR | 20110053506 A | 5/2011 |
| KR | 10-20140090138 A | 7/2014 |
| NL | 7809640 A | 3/1979 |
| TW | 200836649 A | 9/2008 |
| TW | M413347 U | 10/2011 |
| UA | 88052 C2 | 9/2009 |
| WO | WO-9406314 A | 3/1994 |
| WO | WO-9418860 A | 9/1994 |
| WO | WO-9501137 A1 | 1/1995 |
| WO | WO-9741744 A1 | 11/1997 |
| WO | WO-97/048293 A1 | 12/1997 |
| WO | WO-9748295 A1 | 12/1997 |
| WO | WO-9963844 A1 | 12/1999 |
| WO | WO-0028843 A1 | 5/2000 |
| WO | WO-0170054 A | 9/2001 |
| WO | WO-03/025527 A2 | 3/2003 |
| WO | WO-03068300 A1 | 8/2003 |
| WO | WO-03082031 A1 | 10/2003 |
| WO | WO-2004041007 A2 | 5/2004 |
| WO | WO-2004064548 A1 | 8/2004 |
| WO | WO-2004/089126 A1 | 10/2004 |
| WO | WO-2005/025654 A1 | 3/2005 |
| WO | WO-2005046363 A2 | 5/2005 |
| WO | WO-2006082571 A1 | 8/2006 |
| WO | WO-2007/010411 A2 | 1/2007 |
| WO | WO-2007/012007 A2 | 1/2007 |
| WO | WO-2008/015918 A1 | 2/2008 |
| WO | WO-2009/118085 A1 | 10/2009 |
| WO | WO-2010140841 A2 | 12/2010 |
| WO | WO-2011050964 A1 | 5/2011 |

OTHER PUBLICATIONS

U.S. Appl. No. 12/482,376, filed Jun. 10, 2009, U.S. Pat. No. 8,915,254.
U.S. Appl. No. 12/482,379, filed Jun. 10, 2009, U.S. Pat. No. 8,925,555.
U.S. Appl. No. 13/587,416, filed Aug. 16, 2012, U.S. Pat. No. 9,408,416.
U.S. Appl. No. 13/837,438, filed Mar. 15, 2013, US 2013-0312742.
U.S. Appl. No. 14/578,193, filed Dec. 19, 2014, U.S. Pat. No. 10,834,964.
U.S. Appl. No. 15/165,954, filed May 26, 2016, U.S. Pat. No. 10,244,793.
U.S. Appl. No. 15/165,972, filed May 26, 2016, US 2016-0345631.
U.S. Appl. No. 15/166,001, filed May 26, 2016, US 2016-0262459.
U.S. Appl. No. 15/261,823, filed Sep. 9, 2016, US 2016-0374400.
U.S. Appl. No. 15/368,539, filed Dec. 2, 2016, US 2017-0079331.
U.S. Appl. No. 16/248,852, filed Jan. 16, 2019, US 2020-0221759.
U.S. Appl. No. 16/372,342, filed Apr. 1, 2019, US 2019-0289916.
U.S. Appl. No. 16/434,295, filed Jun. 7, 2019.
Gui, et al. (Jan. 1, 1991) "National College Outstanding Book: Chemical Principles" Chapter 4.7.3 (vol. 1).

* cited by examiner

DEVICES FOR VAPORIZATION OF A SUBSTANCE

CROSS REFERENCE TO RELATED APPLICATIONS

This application is a continuation of U.S. patent application Ser. No. 15/165,954, filed May 26, 2016, which is a continuation-in-part of U.S. patent application Ser. No. 13/837,438, filed Mar. 15, 2013, which is a continuation-in-part of U.S. patent application Ser. No. 13/587,416 filed Aug. 16, 2012, which claims priority to U.S. Provisional Patent Application Ser. No. 61/524,308, filed Aug. 16, 2011, each of which are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are smoking devices, particularly to smoking articles which produce vapor by heat transfer to the cartridge by conduction, convection, and/or radiation for smoke and flavor. The devices and systems described herein include self-contained vaporization devices, and more particularly, low-temperature vaporization devices for use with a vaporizable material such as tobacco and tobacco products. These devices may include an elongated main body with a mouthpiece at one end and an attached tubular casing having a vaporization chamber and a heater. The mouthpiece and the casing may form a unitary unit.

BACKGROUND

Smoking devices, such as cigarette holders and pipes are well known in the art for providing flavored vapor from a smokeable substance to a user for therapeutic and smoking pleasure. However, existing devices used have no control of heating and combustion of the tobacco products. The devices tend to produce toxic, tarry and carcinogenic by-products which are harmful and also impart a bitter and burnt taste to a mouth of a user.

In an effort to overcome these deficiencies, there have been numerous attempts to provide a device structure and the substance for producing vapor for smoking which is free from harmful by-product and would provide a cool and soothing vapor for smoking.

For example, U.S. Patent Application Publication No. 2004/0237974 A1, published on Dec. 2, 2004 for Min discloses a filtering cigarette and cigar holder which removes tar and nicotine from the tobacco smoke.

U.S. Patent Application Publication No. 2004/0031495 A1, published on Feb. 19, 2004 for Steinberg discloses a vaporization pipe with flame filter which uses a flame to vaporize the smoking substance.

U.S. Pat. No. 6,164,287, issued Dec. 26, 2000 to White, describes a smoking device which produces smoke from tobacco at low temperatures, without producing harmful byproducts.

U.S. Pat. No. 4,848,374, issued Jul. 18, 1989 to Chard et al describe a smoking device to vaporize aerosol precursor, an event which precedes condensation to mainstream aerosol precursor by contact with heated surface rather than by hot gases into the mouth of a smoker.

U.S. Pat. No. 4,219,032, issued Aug. 26, 1980 to Tabatznik et al describe a smoking device wherein an extracted smoke is cooled by passing it through a suitable liquid to provide a soothing smoke.

U.S. Pat. No. 4,020,853, issued May 3, 1977 to Nuttall, describes a smoking pipe made of ceramic material such as colored and ornamental porcelain for enhancing the artistic look, and also to provide a circulating air to keep the outer wall of the pipe cool and safe for handling.

U.S. Pat. No. 3,792,704, issued Feb. 19, 1974 to Parker, describes a pipe tobacco smoking system, wherein the pipe and the tobacco capsule are mutually designed to yield a slim-line smoking combination that can be manufactured from relatively low temperature thermoplastic material.

The use of tobacco products and the harmful side effects of smoking tobacco continue to gain increasing attention worldwide. As more regulations come into effect regarding smoking in the work place or in public, interest in developing alternative products is growing significantly. One method of reducing the harmful side effects of smoking is to not burn the tobacco products. This is because many of the harmful analytes, such as Hoffman analytes, obtained from smoking are received due to the burning of the material.

A difficulty of developing and marketing a device that can deliver an aerosolized tobacco product is catering to the user in terms of visual and physical appeal of use. A device that can be used multiple times to aerosolize a variety of different substances while providing similar sensations to the user as those from smoking, such as visual vapor, are desirable. A device and product that can aerosolize a tobacco product and reduce Hoffman analytes and mutagenic compounds delivered to a user as compared to smoking are also desirable.

SUMMARY OF THE DISCLOSURE

Described herein are devices for generating an inhalable aerosol comprising: a mouthpiece, a body; an electronic heater within said body comprising a printed circuit board to heat a viscous vaporizable material to a generate an inhalable aerosol; and a temperature regulator. The inhalable aerosol can accommodate a pod comprising particles that are less than about 2 microns (in their longest dimension—whether length or width or depth) or loose leaf tobacco and other botanicals (no pods).

In one aspect, a resistive heating element and thermistor to monitor and precisely control vaporization temperature are disclosed for use in a device for aerosolizing a material. In some embodiments, the heating element comprises an electronic circuit with power transistor to drive the heater. In certain embodiments, the tail of the electronic circuit solders to a PCB (printed circuit board). In some embodiments, the device comprises aerogel insulation to maintain efficiency and low exposed surface temperature. In certain embodiments, the aerogel is a silica aerogel with reinforcing fibers (e.g., Pyrogel 2250 flexible aerogel blanket). In some embodiments, the device comprises a single button interface wherein the single button interface provides means for on, off and wake from sleep (e.g., pressed to begin heating, turn off heating, and wake from standby mode).

In some embodiments, the electronic heater comprises a polyimide thin film ("flex") printed heater circuit (also or alternatively called a flexible heater circuit). In certain embodiments provide the electronic heater with soldered thermistor element for control loop. In certain embodiments, the device comprises a PID (proportional integral derivative) control loop to control operating temperature.

In some embodiments, the device comprises a magnetic charge connector. In some embodiments, the device comprises time or sensor based standby activation to conserve battery power. This may also or alternatively be called a standby mode. In certain embodiments, sensing means includes accelerometer or other tile/vibration sensor, capacitive (touch) sensor, or monitoring the thermistor to detect if the heater is being loaded by the user puffing on the device.

In some embodiments, the heater is a metallic heater wherein the heater component is heat staked, ultrasonic bonded or over-molded into a high temperature capable plastic component. The processes create a hermetic or dust seal. In some embodiments, a split mouthpiece design is disclosed for use in a device for aerosolizing a material. The half of the split mouthpiece is removable and conforms to contour of the device. In some embodiments, the mouthpiece attaches to the body of the device with rare earth magnet. In some embodiments, the mouthpiece attaches to the body with plastic detent or other similar mechanism. In other embodiments, the mouthpiece is integrated into the device with a hinge, or other mechanism (e.g., a string, or the like). In certain embodiments, the mouthpiece swivels or slides away to reveal the heating chamber. In certain embodiments, the mouthpiece is detached fully from the attachment mechanism for cleaning or replacement but still links to the device ("removably captured").

In another aspect provides an electronic stand-alone vaporizer device for use with loose leaf tobacco and/or other botanicals. In some embodiments, the device comprises a mouthpiece that retracts from said device with a push-push mechanism. In some embodiments, the push-push mechanism also turns the device on via a magnet embedded in the mouthpiece and a hall effect sensor on the PCB (printed circuit board). In certain embodiments, the mouthpiece comprises a compression spring, a leaf spring and a stainless steel tube attached to the mouthpiece with a catch groove and a toggle slider. In some embodiments, the device comprises a magnetic on/off control using reed or hall effect switch. In certain embodiments, the magnetic control is integrated into mouthpiece to eliminate additional buttons. In some embodiments, the mouthpiece adapts push-push mechanism for mouthpiece withdrawal and/or retraction. In some embodiments, the device comprises a magnetic lid to cover vaporization chamber. In some embodiments, the device comprises a thermally conductive shell to distribute excess heat and maintain low exposed surface temperature. In some embodiments, the device comprises a button-operated temperature selection with visual, audible indicator, and/or other sensory output (e.g. vibration). In some embodiments, the mouthpiece is integrated into the device with a hinge, or other mechanism (e.g., a string, or the like). In some embodiments, the vaporization device comprises a thin wall metal heating chamber. Thin walls allow for low thermal mass and thus fast startup. In some embodiments, the devices comprise a tilting lid using magnetic or snap attachments for the lid to stay in its closed position to prevent accidental opening. The tilting lid has no visible removal button.

In another aspect provides a device which emulates smoking wherein the device generates an aerosol for inhalation by a subject by heating a viscous material containing plant matter to about 150° C. and wherein the aerosol has a tactile response in the mouth or respiratory tract. The viscous material can comprise an aerosol-forming medium that can comprise at least one of propylene glycol and glycerin to produce a visual aerosol when heated. The viscous material can also comprise tobacco and flavorants.

The device can also deliver an active element to a user that is part of the aerosol. The active element can be absorbed in the respiratory tract. The aerosol can comprise particles less than about 2 microns in diameter.

The target temperature for heating the viscous material in the device can be about 100° C. to about 200° C. Preferably, the target temperature is about 150° C., which generates an aerosol.

In another aspect, a method of creating a tactile response in the mouth or respiratory tract is disclosed. The method comprises: deploying a smoke emulating device wherein the device generates a smokeless aerosol having a tactile response in the mouth or respiratory tract by heating a viscous material containing plant matter contained therein; heating the viscous material to a target temperature; generating an aerosol having the tactile response in the mouth or respiratory tract from the heated viscous material; and inhaling the aerosol. The viscous material can comprise an aerosol-forming medium that can comprise at least one of propylene glycol and glycerin to produce a visual aerosol when heated. The viscous material can also comprise at least one of tobacco and flavorants. The device can deliver an active element to a user that is part of the aerosol. The active element can be absorbed in the respiratory tract.

Provided herein are devices for generating an inhalable aerosol comprising: a mouthpiece; a body; an electronic heater comprising a heater circuit, an oven, and a printed circuit board within said body, said electronic heater configured to heat a viscous vaporizable material and generate an inhalable aerosol; and a temperature regulator.

In some embodiments, the mouthpiece is split or integrated into the device. In some embodiments, the mouthpiece retracts from the device with a push-push mechanism.

In some embodiments, the heater circuit is soldered to the heater circuit board. In some embodiments, the electronic heater comprises a resistive heating element and a thermistor configured monitor and precisely control vaporization temperature of the viscous vaporizable material. In some embodiments, the heater circuit is a thin film polyimide heater.

In some embodiments, the electronic heater is sealed by a hermetic or dust seal.

In some embodiments, the device comprises a magnetic control using reed or hall effect switch. In some embodiments, the magnetic control using reed or hall effect switch is integrated into the mouthpiece.

In some embodiments, the device comprises a magnetic lid.

In some embodiments, the device comprises a thermally conductive shell configured to distribute excess heat and configured maintain a low exposed surface temperature.

In some embodiments, the device comprises time based or sensor based standby mode activation. In some embodiments, the sensor comprises an accelerometer or other tactile/vibration sensor, capacitive (touch) sensor, or a sensor for monitoring the thermistor configured to detect if the heater is being loaded by the user puffing on the device.

In some embodiments, the device comprises a proportional integral derivative (PID) control loop configured to control operating temperature.

In some embodiments, the device comprises a thin wall metal heating chamber.

In some embodiments, the device comprises aerogel insulation. In some embodiments, the aerogel insulation comprises a silica aerogel with reinforcing fibers.

In some embodiments, the heater is thermal pressed, ultrasonic bonded or over-molded into a high temperature capable plastic component. In some embodiments, the heater is heat stated or heat swaged into a high temperature capable plastic component. In some embodiments, the heater is heat swaged into a high temperature capable plastic component.

In some embodiments, the device further comprise a magnetic charge connector configured to connect the device to a charger.

In some embodiments, the device comprises a single button interface.

In some embodiments, the viscous vaporizable material is in a removable pod. In some embodiments, the removable pod comprises particles of the viscous vaporizable material that are less than about 2 microns. In some embodiments, the removable pod comprises the viscous vaporizable material consisting essentially of particle sizes that are less than about 2 microns.

Provided herein is a device for generating an inhalable aerosol comprising: a mouthpiece; a body; an electronic heater within said body configured to heat a viscous vaporizable material and generate an inhalable aerosol; a temperature regulator and an aerogel insulation.

Provided herein is a device for generating an inhalable aerosol comprising: a mouthpiece; a body; an electronic heater within said body configured to heat a viscous vaporizable material and generate an inhalable aerosol; a temperature regulator and a magnetic charge connector.

Provided herein is a device for generating an inhalable aerosol comprising: a mouthpiece; a body; an electronic heater within said body configured to heat a viscous vaporizable material and generate an inhalable aerosol; a battery; a temperature regulator, and time or sensor based standby activation configured to conserve battery power.

Provided herein is a device for generating an inhalable aerosol comprising: a mouthpiece; a body; an electronic heater within said body configured to heat a viscous vaporizable material and generate an inhalable aerosol; a battery; a temperature regulator, and a temperature control loop.

Provided herein is a device for generating an inhalable aerosol comprising: a mouthpiece; a body; an electronic heater within said body configured to heat a viscous vaporizable material and generate an inhalable aerosol; a battery; a temperature regulator, and a single button interface.

Provided herein is a device for generating an inhalable aerosol comprising: a mouthpiece; a body; an electronic heater within said body configured to heat a viscous vaporizable material and generate an inhalable aerosol; a battery; a temperature regulator; wherein the electronic heater is sealed by a hermetic or dust seal.

Provided herein is a device for generating an inhalable aerosol comprising: a mouthpiece; a body; a vaporization chamber; an electronic heater within said body configured to heat a viscous vaporizable material and generate an inhalable aerosol; a temperature regulator; and a magnetic lid configured to cover the vaporization chamber.

Provided herein is a device for generating an inhalable aerosol comprising: a mouthpiece; a body; an electronic heater within said body configured to heat a viscous vaporizable material and generate an inhalable aerosol; a thermally conductive shell configured to distribute excess heat and maintain a low exposed surface temperature; and a temperature regulator.

Provided herein is a device for generating an inhalable aerosol comprising: a mouthpiece; a body; an electronic heater within said body configured to heat a viscous vaporizable material and generate an inhalable aerosol; and a temperature regulator; and a push-push mechanism configured to toggle the mouthpiece between a retracted and an "on" position.

Provided herein is a device for generating an inhalable aerosol comprising: a mouthpiece; a body; an electronic heater within said body configured to heat a viscous vaporizable material and generate an inhalable aerosol; a temperature regulator; and a button-operated temperature selection with a visual indicator, an audible indicator and/or a vibration indicator.

Provided herein is a device for generating an inhalable aerosol comprising: a mouthpiece; a body; an electronic heater within said body configured to heat a viscous vaporizable material and generate an inhalable aerosol; a temperature regulator; and a tilting lid comprising a magnetic attachment or a snap attachment configured to maintain the lid in its closed position and/or configured to prevent accidental opening.

Provided herein is a device for generating an inhalable aerosol comprising: a mouthpiece; a body; an electronic heater within said body configured to heat a viscous vaporizable material and generate an inhalable aerosol; and a temperature regulator, wherein the mouthpiece is integrated into the device.

Provided herein is a device for generating an inhalable aerosol comprising: a mouthpiece; a body; an electronic heater comprising a heater circuit within said body configured to heat a viscous vaporizable material and generate an inhalable aerosol; and a temperature regulator; wherein heater circuit has low resistance such that a single battery is capable of powering the device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 2:
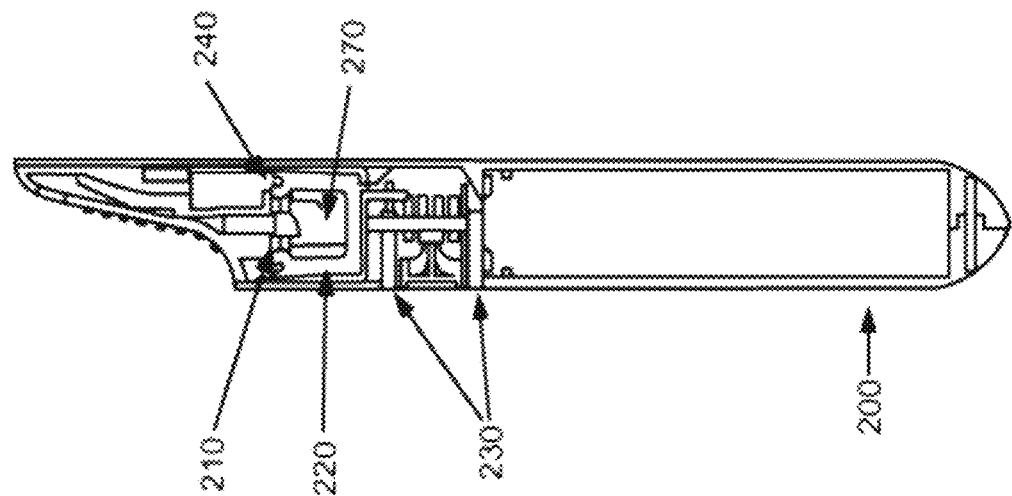
FIG. 2 is an interior view of the same embodiment as shown in FIG. 9, shown as a section taken through the charging contacts 312 in the long axis of the device.

The devices and systems described herein have a wide range of applications for inhalation of an active substance as will be appreciated by persons of skill in the art upon reviewing the disclosure. For example, the devices, cartridges (i.e. pods), such as disclosed in U.S. application Ser. No. 11/485,168, systems, kits and methods could be used, for example, to inhale a tobacco product through the mouth or nose. The devices, systems, kits and methods could be used, for example, to inhale any substance, such as a botanical, pharmaceutical, nutraceutical, or any other substance providing a benefit or sensation to an end user.

Provided herein is a device for generating an inhalable aerosol comprising: a mouthpiece 110; a body; an electronic heater comprising a heater circuit, an oven, and a printed circuit board within said body, said electronic heater configured to heat a viscous vaporizable material and generate an inhalable aerosol; and a temperature regulator.

In some embodiments, the mouthpiece is split or integrated into the device. In some embodiments, the mouthpiece retracts from the device with a push-push mechanism.

In some embodiments, the heater circuit is soldered to the heater circuit board. In some embodiments, the electronic heater comprises a resistive heating element and a thermistor configured monitor and precisely control vaporization temperature of the viscous vaporizable material. In some embodiments, the heater circuit is a thin film polyimide heater.

In some embodiments, the electronic heater is sealed by a hermetic or dust seal.

In some embodiments, the device comprises a magnetic control using reed or hall effect switch. In some embodiments, the magnetic control using reed or hall effect switch is integrated into the mouthpiece.

In some embodiments, the device comprises a magnetic lid.

In some embodiments, the device comprises a thermally conductive shell configured to distribute excess heat and configured maintain a low exposed surface temperature.

In some embodiments, the device comprises time based or sensor based standby mode activation. In some embodiments, the sensor comprises an accelerometer or other tactile/vibration sensor, capacitive (touch) sensor, or a sensor for monitoring the thermistor configured to detect if the heater is being loaded by the user puffing on the device.

In some embodiments, the device comprises a proportional integral derivative (PID) control loop configured to control operating temperature.

In some embodiments, the device comprises a thin wall metal heating chamber.

In some embodiments, the device comprises aerogel insulation. In some embodiments, the aerogel insulation comprises a silica aerogel with reinforcing fibers.

In some embodiments, the heater is thermal pressed, ultrasonic bonded or over-molded into a high temperature capable plastic component. In some embodiments, the heater is heat stated or heat swaged into a high temperature capable plastic component. In some embodiments, the heater is heat swaged into a high temperature capable plastic component.

In some embodiments, the device further comprise a magnetic charge connector configured to connect the device to a charger.

In some embodiments, the device comprises a single button interface.

In some embodiments, the viscous vaporizable material is in a removable pod. In some embodiments, the removable pod comprises particles of the viscous vaporizable material that are less than about 2 microns. In some embodiments, the removable pod comprises the viscous vaporizable material consisting essentially of particle sizes that are less than about 2 microns.

Figure 1:
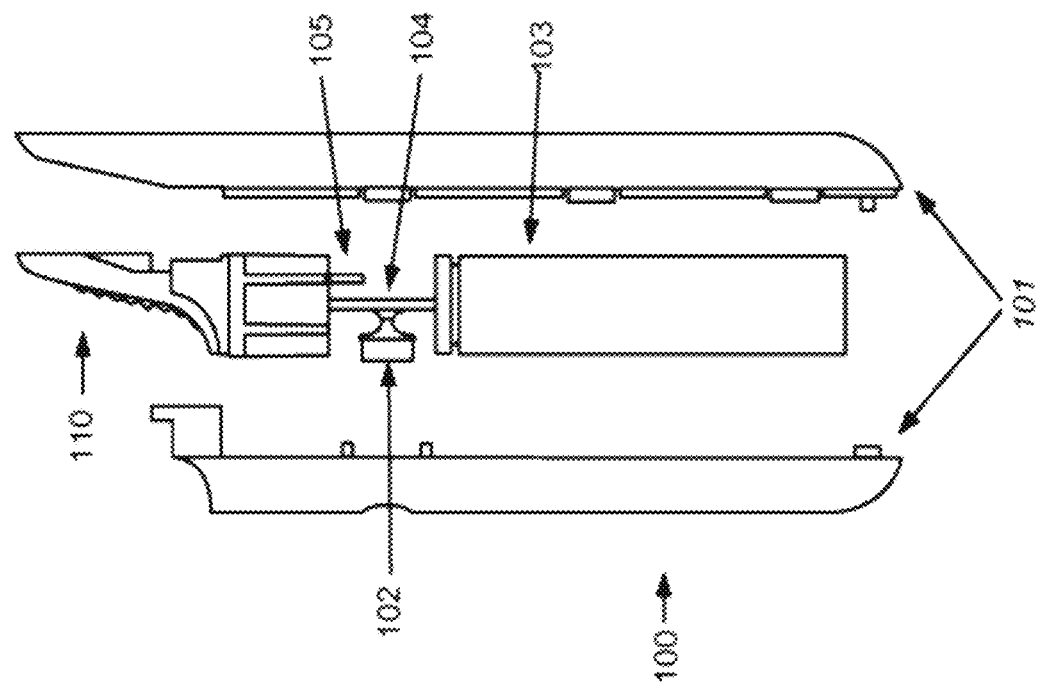
FIG. 1 illustrates a device comprising a single button interface, a LiPo battery, and body outer halves wherein the tail of flexible heater circuit is soldered to a PCB.
Figure 3B:
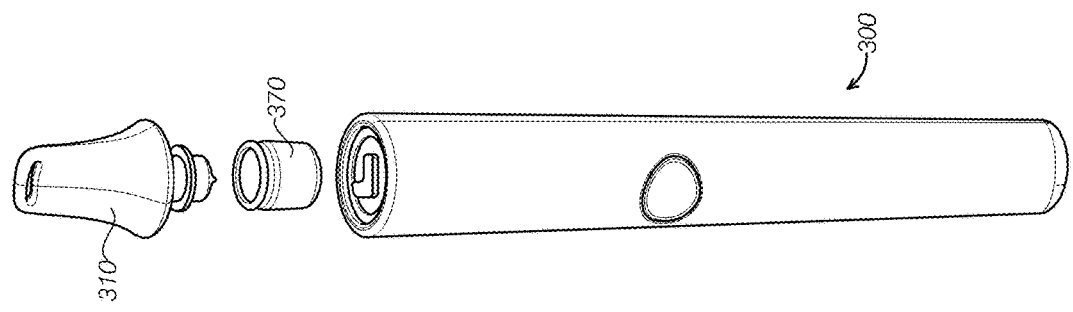
FIGS. 3A and 3B are perspective views of the device with detachable mouthpieces and a tactile button with LED-illuminated "halo" indicator.
Figure 3A:
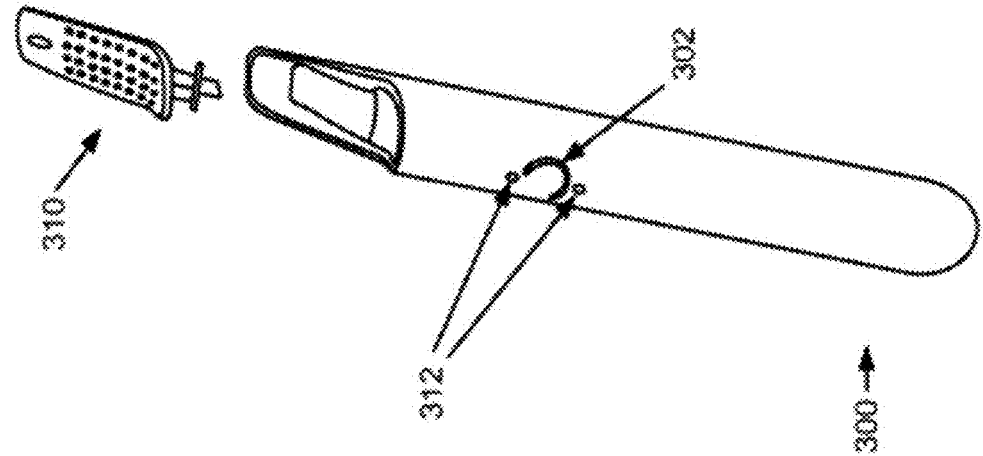

Provided herein is a device for generating an inhalable aerosol comprising: a mouthpiece 110; a body; an electronic heater within said body configured to heat a viscous vaporizable material and generate an inhalable aerosol; a battery; a temperature regulator, and a single button interface. An exemplary device 100 is illustrated in FIG. 1 comprising a single button interface 102 for on, off, wake from sleep mechanism and a heater circuit (105, tail shown) soldered to a PCB 104 and a battery 103 (e.g., a LiPo battery). As shown in FIG. 1, body outer halves 101 snap together to hold and protect the device. In some instances, the outer body is molded as one part. In some embodiments, the single button interface that provides mechanism for on, off and wake from sleep. In other embodiments, additional buttons are included for any of these functions. For example, pressing the single button for 1 second turns the device on. Continuing to hold the button for 5 seconds disables the motion-based low power standby and automatic shut-down. Alternatively, a second button may be used to disable the motion-based low power standby and and/or shut-down. If a user does not want the device to cool down while resting on a table, e.g., they can use this override. In some embodiments, upon power-up, if the single button is depressed for a very long period (>10 seconds), the device turns off again. This is to prevent inadvertent activation while in a purse, etc. While on, pressing the button momentarily turns it off. In some embodiments, a single or more than one button could report battery level (via LED blinks, for instance), change operating temperature of the device, or change the nominal intensity of the LED(s)—if the user is in a dark environment and does not want the light to be distracting. These various features could be triggered with one or more buttons or with the same button by pressing it for a prescribed duration or number of presses. Thus, a single button interface may include a single button that is configured to be pressed to begin heating, select a heating temperature, and turn off heating.

As described herein, an electronic heater comprises a heater circuit, an oven and a printed circuit board to heat a viscous vaporizable material to a generate an inhalable aerosol. The heater circuit may be flexible. In some embodiments, flexible heater circuits are typically etched from a copper- or constantan-clad polyimide film. In some embodiments, a flexible heater is constructed by stamping (die-cutting) a thin sheet of constantan or copper. In this case, the heater circuit would have to be electrically insulated from adjacent conductive elements in the assembly, using polyimide or other suitable insulation that is stable at elevated temperatures. The heater circuit heats the attached oven which then heats the cartridge or active substance by thermal conduction. The resistive heater circuit heats up as current passes through it. Heat is then conducted from the circuit to the oven walls. Thermal conduction continues from the oven walls into the cartridge or active substance. Note that heat also transfers from the oven walls into the active substance or cartridge via convection and radiation, but most transfer occurs via conduction.

In some embodiments, the device comprises more than one button interface for on, off, wake from sleep mechanism and a heater circuit soldered to a PCB.

Provided herein is a device for generating an inhalable aerosol comprising: a mouthpiece; a body; an electronic heater within said body configured to heat a viscous vaporizable material and generate an inhalable aerosol; a battery;

a temperature regulator, and time or sensor based standby activation configured to conserve battery power. In some embodiments, the device comprises time or sensor based standby activation to conserve battery power. This may also or alternatively be called a standby mode. The standby mode may also or alternatively be called sleep, or sleep mode. After non-use based on time, movement or lack thereof, position (e.g. vertical), or placement in a charging cradle, or after any combination of any of these, the device is programmed to convert to sleep mode (standby mode), in order to conserve battery power, at least. The device may be awoken from this standby or sleep mode by a change in any of: movement (e.g. horizontal from vertical, vertical from horizontal, or movement indicating the user has picked up the device), removal from the charging cradle, user touch, the user puffing on the device, or activation by pressing any button on the device (or any combinations thereof). After an extended period in standby mode, the device will turn off, to be awoken and/or turned on by the user pressing the button on the device, in some embodiments, or by the user puffing on the device. In such an embodiment, simply moving the device or removing it from its charging cradle will not activate the device once turned off. In other embodiments, moving the device or removing it from its charging cradle does turn on the device from off or standby mode.

In some embodiments, standby mode conserves battery power by lowering the regulation temperature of the device. For example, a large portion of the heat generated by the device is lost to the environment, whether or not the user is puffing on it. So maximizing the time the device spends in standby, and minimizing the internal temperature while it's in standby conserve power. However, when the device awakes from standby, it is desirable for it to return to the main operating temperature as quickly as possible, so as to give the impression of an uninterrupted puffing experience to the user. So a balance must be established. For example, on the current electronic cartridge-based device, the main operating temperature is 165° C., and standby temperature is 150° C. This temperature difference is slight enough that if the user wakes the device from standby, by the time the user starts puffing, the heater has had enough time to raise the temperature and the user perceives little or no interruption in production of vapor. In some embodiments, the temperature difference is set to be 30° C., 25° C., 20° C., 15° C., 10° C., or 5° C. between the main operating temperature and standby temperature. In some embodiments, the temperature difference is set to be any temperature from 30° C. to 5° C. between the main operating temperature and standby temperature.

In some embodiments, the battery is a disposable battery. In other embodiments, the battery is a rechargeable battery. In certain embodiments, the rechargeable battery is a lead-acid, nickel cadmium (NiCd), nickel metal hydride (NiMH), lithium ion (Li-ion), lithium ion polymer (Li-ion polymer or LiPo), or the like.

A rechargeable battery, storage battery, or accumulator is a type of electrical battery. It comprises one or more electrochemical cells, and is a type of energy accumulator. It is known as a secondary cell because its electrochemical reactions are electrically reversible. Rechargeable batteries come in many different shapes and sizes, ranging from button cells to megawatt systems connected to stabilize an electrical distribution network. Several different combinations of chemicals are commonly used, including: lead-acid, nickel cadmium (NiCd), nickel metal hydride (NiMH), lithium ion (Li-ion), and lithium ion polymer (Li-ion polymer, Li-poly, Li-Pol, LiPo, LIP, PLI or LiP).

The device is capable of creating temperatures high enough to aerosolize a product contained within the device. An exemplary device can comprise a mouthpiece and a body having a heater, an oven chamber, a LiPo battery, and a controller for maintaining the operating temperature. A user-selected temperature, as described above, could be used as an input to this system. In some embodiments, the temperature could be pre-set. Examples of operating temperature regulators of a device include a bimetallic actuator. Alternatively, a system could be employed to measure the current temperature, for example, with a thermocouple sensor and compare it to a prescribed temperature, for example, with a micro-controller, and by controlling an electromechanical valve, for example, servo or solenoid valve. A user-selected temperature, as described above, the selected temperature could be used as an input to this system. Typically, the operating temperatures of the device are no more than 200° C.

Provided herein is a device for generating an inhalable aerosol comprising: a mouthpiece; a body; an electronic heater within said body configured to heat a viscous vaporizable material and generate an inhalable aerosol; a battery; a temperature regulator, and a temperature control loop. In certain embodiments provide the heater with soldered thermistor element for control loop. In certain embodiments, the device comprises a PID (proportional integral derivative) control loop to control operating temperature. The control loop serves to precisely regulate the desired setpoint temperature for the device. Depending on the design and intended use of the device, the set point temperature, in some embodiments, is fixed; in other embodiments, the set point temperature is user-selectable. The set point can also change dynamically during device operation. For example, in standby mode the set point is lowered a certain amount. In some embodiments, the input for the control loop is typically a thermistor, located on or adjacent to the heater circuit. This thermistor leads to a microcontroller which makes A/D measurements and the resulting value is used in calculating the PID control variable. The control variable then sets the duty cycle (and resulting power output) of the heater circuit.

Provided herein is a device for generating an inhalable aerosol comprising: a mouthpiece; a body; an electronic heater comprising a heater circuit within said body configured to heat a viscous vaporizable material and generate an inhalable aerosol; and a temperature regulator; wherein the heater circuit has low resistance such that a single battery is capable of powering the device. In some embodiments, the heater circuit is of such low resistance that a single battery may be used to power the device. In some embodiments, the heater circuit resistance is chosen such that the power output of the heater circuit is high enough to reach the desired operating temperature, within an acceptable heat-up period, and such that it can withstand the loading of the system by a user puffing on the device. A rough calculation is provided by the relation: $R = V^2/P$, where V is the battery voltage under load, P is the desired wattage of the heater, and R is the heater circuit resistance.

Provided herein is a device for generating an inhalable aerosol comprising: a mouthpiece; a body; an electronic heater within said body configured to heat a viscous vaporizable material and generate an inhalable aerosol; a battery; a temperature regulator; wherein the electronic heater is sealed by a hermetic or dust seal. As illustrated in FIG. 10, an exemplary device 200 comprises a thin-walled stainless steel tube 210 perforated the sealed lid of the capsule (i.e., a pod). The thin-walled stainless steel tube 210 (e.g. a metallic "oven") in the illustrated device is thermal pressed (e.g., heat staked or swaged), ultrasonic bonded or overmolded into a high temperature capable plastic component. The processes create a hermetic or dust seal (air-tight seal) 240, which prevents environmental dust from entering the internal chambers of the device, as well as any dust from the internal insulation materials from escaping the device and entering the heating chamber. The plastic component may comprise any thermoplastic materials that provide high temperature stability. In some embodiments, the plastic component comprises polyphenylene sulfide (PPS, trade name Ryton), polyetherimide (PEI, trade name Ultem), liquid crystal polymer (LCP), or the like. In certain embodiments, the plastic component comprises PPS. PPS is used also for its general good moldability.

In certain embodiments, the oven is heat staked or heat swaged into a high temperature capable plastic component. As referring herein, with heat swaging, material is formed all the way around the perimeter of the mating edge. With heat staking, there would have a few posts of the thermoplastic that insert through holes in the formed metal oven, and then the posts are heated to form "rivets" of a sort). In certain embodiments, the oven is heat swaged into a high temperature capable plastic component. In some embodiments, the oven is bonded to the plastic component using adhesive. In certain embodiments, the adhesive is stable at high temperatures, such that the adhesive is not soften or off-gas. In some embodiments, the oven is joined to the plastic component by mechanical mechanism, such as using a crimp threaded connection, press fit, or the like. For any mechanical joining, in some embodiments, an o-ring is used between the two components to ensure the dust seal is created. It is important to minimize the thermal transfer at this junction, since that's how a lot of heat is transferred to the outer casing of the device (and thus, lost to the environment).

Provided herein is a device for generating an inhalable aerosol comprising: a mouthpiece; a body; an electronic heater within said body configured to heat a viscous vaporizable material and generate an inhalable aerosol; a temperature regulator and an aerogel insulation. In some embodiment the aerogel insulation is an aerogel blanket. In some embodiments, the device comprises an insulation chamber 220 that includes an aerogel blanket (not shown in FIG. 2, see FIG. 5) to maintain efficiency and low exposed surface temperature. In some embodiments, the aerogel may be a silica aerogel with reinforcing fibers (e.g., Pyrogel 2250 flexible aerogel blanket).

As provided herein, the term, "aerogel" refers to a synthetic porous material derived from a gel, in which the liquid component of the gel has been replaced with a gas. The result is a solid with extremely low density and thermal conductivity. Aerogels are good thermal insulators because they almost nullify the three methods of heat transfer (convection, conduction, and radiation). They are good conductive insulators because they are composed almost entirely from a gas, and gases are very poor heat conductors. Silica aerogel is especially good because silica is also a poor conductor of heat (a metallic aerogel, on the other hand, would be less effective). They are good convective inhibitors because air cannot circulate through the lattice. Silica aerogel is the most common type of aerogel and the most extensively studied and used. It is a silica-based substance, derived from silica gel. Carbon aerogels are composed of particles with sizes in the nanometer range, covalently bonded together. They have very high porosity (over 50%, with pore diameter under 100 nm) and surface areas ranging between 400-1,000 m2/g. Aerogels made with aluminum oxide are known as alumina aerogels. These aerogels are used as catalysts, especially when "doped" with a metal different from Al. Nickel-alumina aerogel is the most common combination.

In some embodiments, the device also include two magnets 230 (e.g., gold-plated rare earth magnets, or the like) used as both mechanical attachment and battery charging conduits to a charging cradle (not shown). The magnets need to strong enough to hold the device in place in the charging cradle. In some embodiments, the magnets comprise NdFeB, grade N42. In some embodiments, the magnets have 6128 gauss of surface field. The pod 270 is inserted into the oven, which has a polyimide thin film heater and thermistor applied to its exterior. A polyimide thin film heater is constructed of a thin, high dielectric, lightweight organic polymer film which provides excellent tensile strength, tear resistance and dimensional stability.

Thus, provided herein is a device for generating an inhalable aerosol comprising: a mouthpiece; a body; an electronic heater within said body configured to heat a viscous vaporizable material and generate an inhalable aerosol; a temperature regulator and a magnetic charge connector.

In some embodiments, the battery used in the device is a single cell LiPo battery (e.g., 18-650 size 2600 mAh lithium ion single cell or 14-650 size 940 mAh lithium ion single cell) for repeated uses of the device. In some embodiments, the battery used for the device is other suitable rechargeable battery with 18-650 size 2600 mAh or 14-650 size 940 mAh. The device can be used for up to 10, 20, 30, 40, 50, 60 or more uses (depending what size of the rechargeable battery is employed). In some embodiments, the device can be used for more than 60 uses. The device can also be used for up to 1, 2, 3, 4, 5, 6, 7, or 8 hours or more of continuous or non-continuous use. A cartridge for use with the device can be disposed after each use or used for multiple uses. The long lasting use of a device provides the user the advantage of not having to service the device or recharge the battery on a regular basis.

Typically, the operating temperatures of the device are no more than 200° C. Often the temperature required to aerosolize a product is between about 100 to 200° C. In some embodiments, the temperature required to aerosolize a product is about 150° C. Once the product within the device has been aerosolized, the aerosolized product is provided to a user through a mouthpiece. In many cases, an exemplary device is designed to emulate a smoking device, such as a cigarette, a pipe or a cigar holder.

In FIGS. 3A and 3B, the exemplary devices 300 comprises a split mouthpiece (310) design where half is removable and conforms to contour of the device. In some embodiments, the mouthpiece attaches to body with rare earth magnet. In some embodiments, the mouthpiece attaches to body with plastic detent or other mechanism. In FIG. 3B, the pod 370 is shown being inserted into the oven with the mouthpiece 310 detached.

Provided herein is a device for generating an inhalable aerosol comprising: a mouthpiece; a body; an electronic heater within said body configured to heat a viscous vaporizable material and generate an inhalable aerosol; and a temperature regulator, wherein the mouthpiece is integrated into the device.

In some embodiments, the mouthpiece is integrated into the device with a hinge, or other mechanism (such as a string, or the like). In certain embodiments, the mouthpiece swivels or slides away to reveal the heating chamber. In certain embodiments, the mouthpiece is detached fully from the attachment mechanism for cleaning or replacement but is still linked to the device ("removably captured"). In some embodiments, the device also includes magnetic charge contacts 312 and a tactile button 302 with LED-illuminated "halo" indicator. The indicator reports information about the state of the device. In some embodiments, a saw-tooth pattern indicates that it is heating up. In some embodiments, solid pattern indicates that the set point temperature has been reached and the user can start puffing on the device. If the battery is critically low, in some embodiments, the LED indicator flashes several times (e.g., 5 times) and then the devices turn off. In some embodiments, while shaking the device, the motion sensor detects this and the LED indicates current battery level: for example, 3 flashes for full charge, 2 flashes for partial charge, and 1 flash for low charge. The device then resumes normal operation. When the device is placed in a charge cradle, in some embodiments, a saw-tooth pattern indicates that it is charging. In certain embodiments, when charging is complete, the LED turns solid. In some embodiments, error states can also be reported: if an internal failure is determined, the indicator flashes 10 times and the device turns itself off.

In some embodiments, the device comprises a detachable mouthpiece which can attach and/or insert into a removable pod. The mouthpiece is removed by quarter-turn to expose the removable pod. The removable pod comprises tobacco and/or other botanicals for use to generate an inhalable aerosol. The pod, in some embodiments, comprises particles less than about 2 microns in diameter. In some embodiments also provides vaporization devices for use with a viscous vaporizable material such as loose leaf tobacco and other botanicals (no pods).

Figure 4:
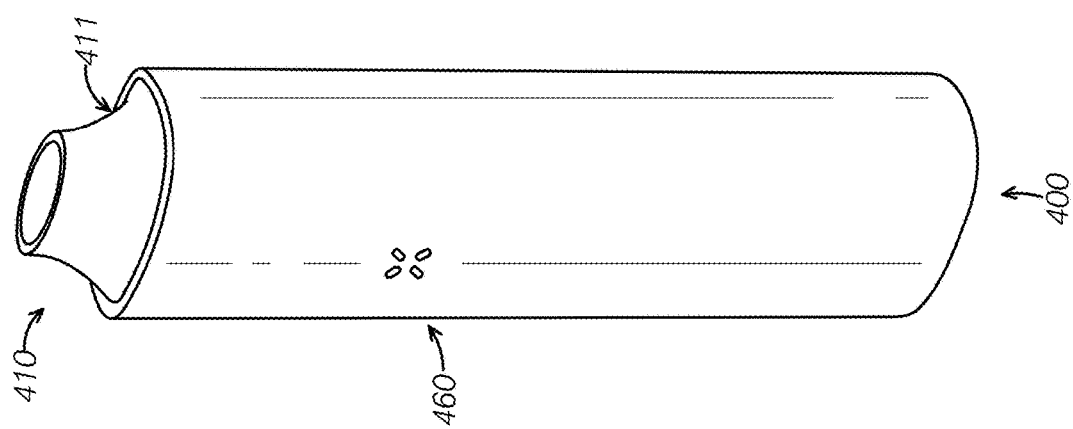
FIG. 4 demonstrates a device of single piece with extruded aluminum outer body wherein the mouthpiece of the device retracts from device with a push-push mechanism.

FIG. 4 demonstrates exemplary devices (400) with a mouthpiece 410 retracted from device with a push-push mechanism. This also turns the devices on via a magnet embedded in the mouthpiece 411, and a hall effect sensor on the PCB. The devices include a LED indicator 460, (or the like) and a single piece extruded aluminum outer body. In some embodiments, the LED indicator is a tri-color (RGB). In some embodiments, the LED indicator displays many colors. For example, when heating, the indicator glows purple. Once the set point temperature is reached, it glows green. When in standby, it glows blue. If the device is shaken, battery indications are 3 blinks, and color determines the charge level: green for full charge, yellow for partial, and red for low. If the mouthpiece is removed fully from the device, the device immediately stops heating and the LED indicates the current user-selectable temperature setting: red for high, orange for medium, yellow for low temperature. Pressing the "temp set button" revealed by removing the mouthpiece cycles the temperature setting in firmware, and the new setting is reflected on the LED. Upon reinserting the mouthpiece, the device returns to normal heating operation. While charging, the LED is solid orange. When charging is complete, it turns solid green. Similar to the other embodiments, the LED can also report error states by flashing and/or distinct color of flashes. The colors described above may be changed to any colors in accordance with the practice of this invention.

In some embodiments, the device comprises a mouthpiece that retracts from said device with a push-push mechanism. In some embodiments, the push-push mechanism also turns the device on via a magnet 514 embedded in the mouthpiece and a hall effect sensor on the PCB (printed circuit board). One of ordinary skill in the art would readily recognize other suitable mechanism to turn the device on with suitable sensor.

Figure 5:
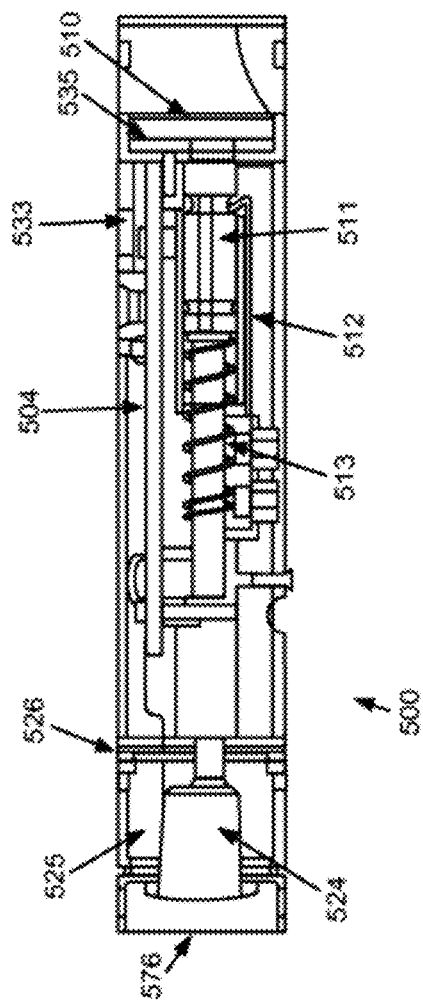
FIG. 5 is a sectional detail view of the device 500 as illustrated in FIG. 12.

Provided herein is a device for generating an inhalable aerosol comprising: a mouthpiece; a body; an electronic heater within said body configured to heat a viscous vaporizable material and generate an inhalable aerosol; and a temperature regulator; and a push-push mechanism configured to toggle the mouthpiece between a retracted and an "on" position. An internal view of the exemplary device of FIG. 4 is shown in FIG. 5. In such embodiment comprising a push-push mechanism, the device includes a vaporization chamber lid 576 (opposite of the mouthpiece 510). The device comprises a deep-drawn stainless steel heating chamber 524 ("oven"), with polyimide thin film circuit heater applied. A push-push mechanism for retracting mouthpiece consists of compression spring 513, leaf spring 512, and stainless steel tube 511 attached to the mouthpiece 510, with a catch groove 534 and a toggle slider 509. Reed switch/hall effect sensor 533 is incorporated to detect if mouthpiece is inserted (device runs off). To extend the mouthpiece into the "on" position, the user presses on the mouthpiece 510. The mouthpiece is attached to the tube 511, so this action compresses the compression spring 513. This action also causes the leaf spring 512 to flex away from the axis of the tube and onto the outer diameter of the toggle slider 509. When the user then releases the mouthpiece, the compression spring pushes the mouthpiece & tube sub-assembly outward from the device. The angled lip of the leaf spring catches on the toggle slider, causing the slider to traverse the tube until it reaches a shoulder on the tube. At this point, the mouthpiece continues to extend out of the device, and the leaf spring now wipes along the toggle slider and continues along the shoulder of the outer diameter of the tube, which is of equivalent diameter and thus poses no resistance. When the catch groove of the tube intersects with the lip of the leaf spring, the mouthpiece stops, and is now in the extended, "on" position. Pressing the mouthpiece from the "on" position uses the push-push mechanism to move the mouthpiece to a retracted position. The push-push mechanism, thus, is configured to toggle the mouthpiece between an "on" position or an extended position such that the mouthpiece is extended from the body of the device, and a retracted position. In some embodiments, in the retracted position, the mouthpiece is fully within the body of the device. In some embodiments, in the retracted position, the mouthpiece is fully within the body of the device but is exposed at the open end of the device. In some embodiments, in the retracted position, the mouthpiece is substantially within the body of the device such that a portion of the mouthpiece extends beyond the end out of the body of the device.

Many devices use a temperature regulation scheme in that the temperature regulator (bimetallic discs or other regulator) are located in close proximity to the area where temperature is most critical (at the oven). See temperature select button 535, PCB 504, O-ring seal 526 to control potential aerogel dusting, and insulation chamber 525 to contain aerogel blanket. Related art has typically located the temperature-sensitive component at the flow valve, which can be easily influenced by the cool temperature of expanding fuel gas and has minimally intimate contact with the vaporizing chamber. Examples of related devices and methods are described in U.S. patent application Ser. No. 11/485,168 (Publication No. US-2007-0283972-A1), U.S. Pat. Nos. 4,819,665, 4,793,365, 5,027,836 and PCT Application Publication No. WO 2006/082571. The regulation scheme of an exemplary device may be tuned to a specific temperature by a simple twist of the oven.

Provided herein is a device for generating an inhalable aerosol comprising: a mouthpiece; a body; an electronic heater within said body configured to heat a viscous vaporizable material and generate an inhalable aerosol; a temperature regulator; and a button-operated temperature selection with a visual indicator, an audible indicator and/or a vibration indicator. In some embodiments, the device comprises a button-operated temperature selection with visual, audible indicator, and/or other sensory output (e.g. vibration). In some embodiments, a tactile (mechanical) switch is used as input to a microcontroller, which, via its software, indicates the change to the user (e.g., by visual LED, audible, vibration, or the like), and changes the set point temperature of the device. The switch can also be capacitive, resistive, or the like.

In some embodiments, the vaporization device comprises a thin wall metal heating chamber (or oven chamber). Thin walls allow for low thermal mass and thus fast startup. When the device use the viscous vaporizable material directly without including them in a pod (or a cartridge), the terms, "heating chamber", "oven chamber" and "vaporization chamber" are used interchangeably. For the device including a pod or a cartridge, the terms, "heating chamber" and "oven chamber" are used interchangeably. In general, as shown in FIGS. 2 and 5, the oven is configured to fit within the housing (and fits within the housing). As shown in these figures, the oven may be adjacent to the mouthpiece or on an opposite side of the elongate body from the mouthpiece.

Figure 6:
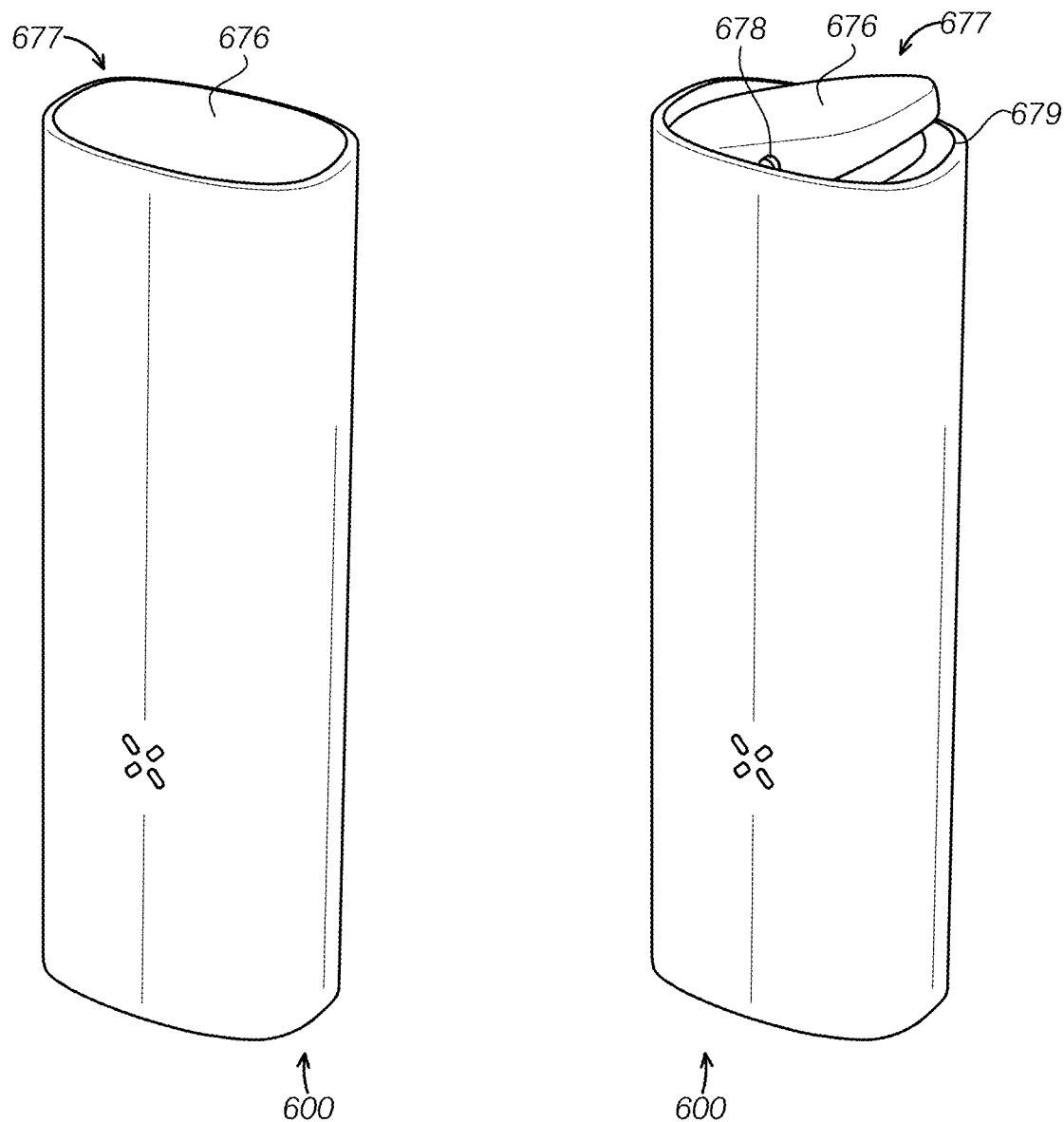
FIG. 6 shows how the magnetically attached vaporization chamber lid works.

Provided herein is a device for generating an inhalable aerosol comprising: a mouthpiece; a body; a vaporization chamber; an electronic heater within said body configured to heat a viscous vaporizable material and generate an inhalable aerosol; a temperature regulator; and a magnetic lid configured to cover the vaporization chamber. In the exemplary devices 600 of FIG. 6, an exemplary magnetically-attached vaporization chamber lid 676 is shown. The lid 676 is nominally recessed entirely into the body of the device. This is to prevent inadvertent removal of the lid in the user's pocket, purse, etc. To remove the lid, the user presses a finger against one side of the oval-shaped lid. The underside of the lid is chamfered, such that this allows the opposite side of the lid to pivot up. Two rare earth magnets are embedded on either side of the lid, along its short axis. Two mating magnets are embedded in the body of the device at corresponding points. These magnets together form a "hinge" around which the lid can swivel 678. Once the lid is swiveled up, it is relatively easy to overcome the magnetic force and remove the lid entirely, allowing access to the vaporization chamber. In some embodiments, the vaporization chamber lid is attached by other mechanism such as screw-on, a snap on, or the like. Thus, in some embodiments, the devices comprise a tilting lid using magnetic or snap attachments for the lid to stay in its closed position to prevent accidental opening. Provided herein is a device for generating an inhalable aerosol comprising: a mouthpiece; a body; an electronic heater within said body configured to heat a viscous vaporizable material and generate an inhalable aerosol; a temperature regulator; and a tilting lid comprising a magnetic attachment 677 or a snap attachment 679 configured to maintain the lid in its closed position and/or configured to prevent accidental opening. In FIG. 6, the elongate body of the device is cylindrical and has an oval cross-section, as shown.

Figure 7:
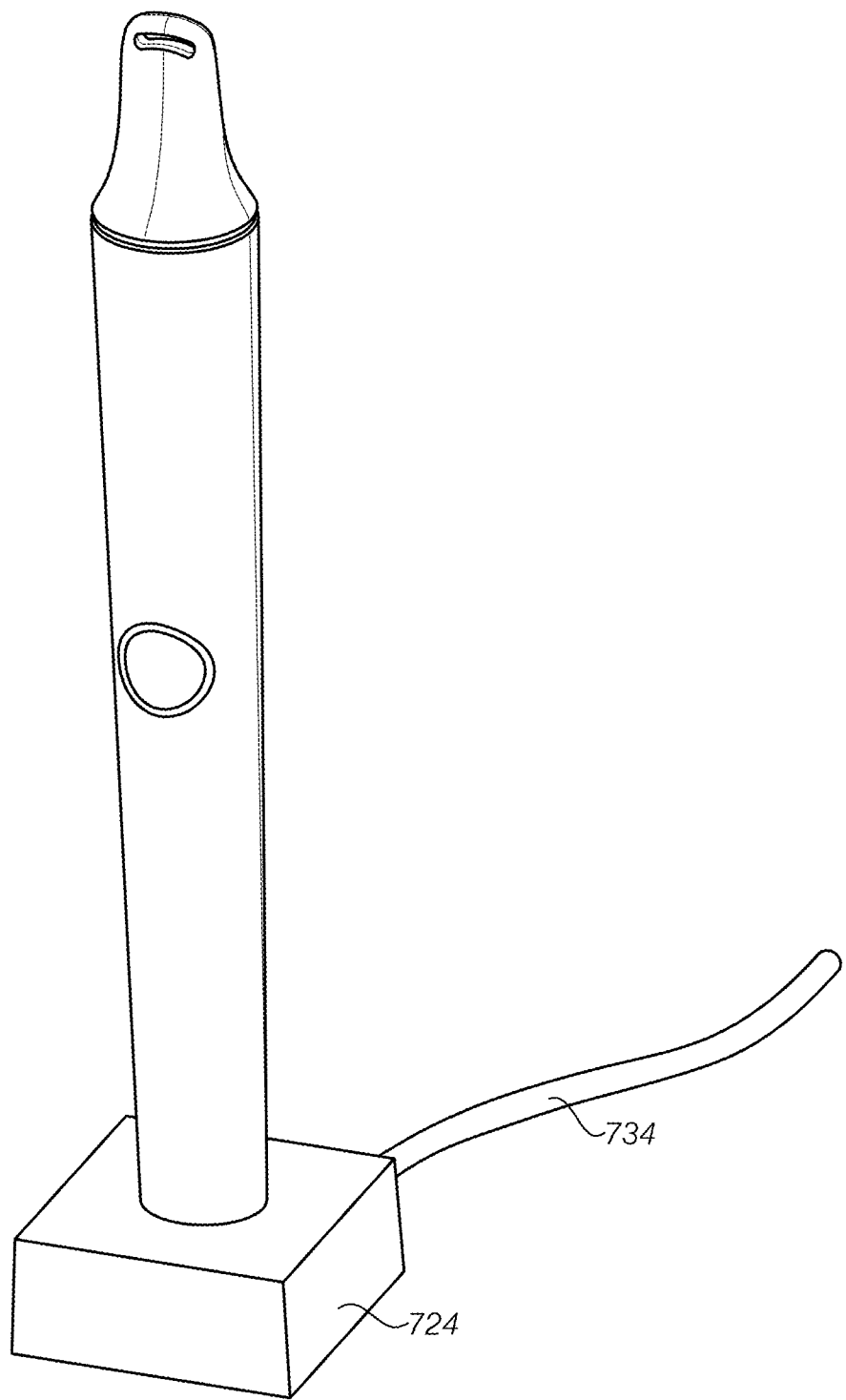
FIG. 7 shows how to charge the battery by an exemplary battery charging source (e.g. a USB charger).

One of ordinary skill in the art would readily employ energy supply sources to charge battery. For example, in FIG. 7, a USB charger 724 with a USB charge cable 734 are shown. In some embodiments, the energy supply source is a wall mount charger. In some embodiments, the energy supply source is a car charger. In some embodiments, the energy supply source is a portable charger. In certain embodiments, the energy supply sources include solar powered, wind powered or other green energy powered chargers.

In some embodiments, the device comprises a thermally conductive shell to distribute excess heat and maintain low exposed surface temperature. In some embodiments, the thermally conductive shell is made of materials having low specific heat but high thermal conductivity. In some embodiments, the configuration of materials in the thermally conductive shell is such that the temperature of the shell is below 140 degrees F., below 130 degrees F., below 120 degrees F., below 110 degrees F., below 100 degrees F., at or below 140 degrees F., at or below 130 degrees F., at or below 120 degrees F., at or below 110 degrees F., at or below 100 degrees F., at or below 98.6 degrees F., at or below 90 degrees F., at or about room temperature, at or below about 140 degrees F., at or below about 140 degrees F., at or below about 130 degrees F., at or below about 120 degrees F., at or below about 110 degrees F., at or below about 100 degrees F., at or below a temperature at which skin will burn after 2 seconds of touch, at or below a temperature at which skin will burn after 5 seconds of touch, at or below a temperature at which skin will burn after 10 seconds of touch, and/or about at room temperature. This combination means heat will spread quickly, but when held there is not much energy to be absorbed into the hand. In some embodiments, the thermally conductive shell is made of aluminum, or the like. Provided herein is a device for generating an inhalable aerosol comprising: a mouthpiece; a body; an electronic heater within said body configured to heat a viscous vaporizable material and generate an inhalable aerosol; a thermally conductive shell configured to distribute excess heat and maintain a low exposed surface temperature; and a temperature regulator.

Figure 8:
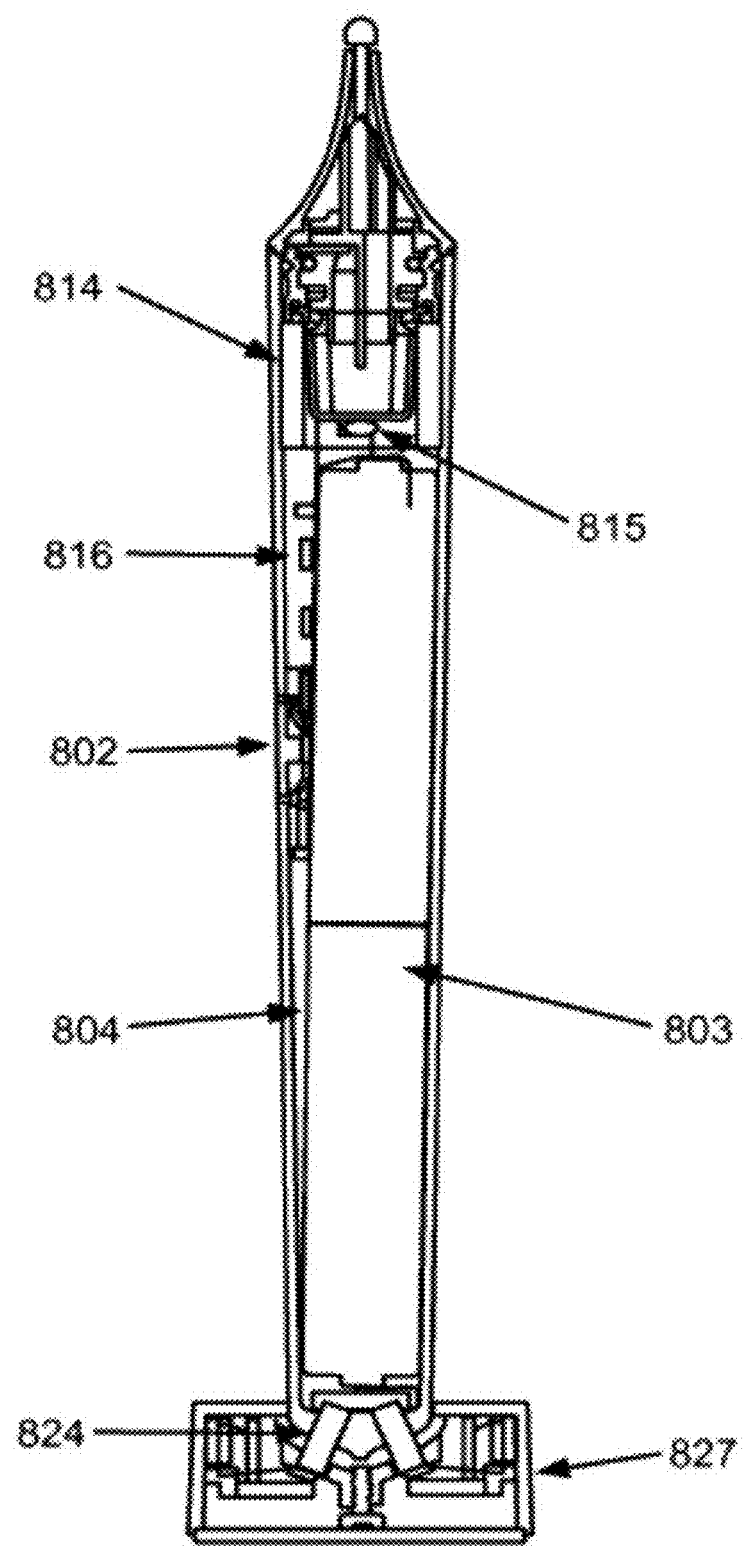
FIG. 8 is an interior detail view of the device charged by a USB charger shown in FIG. 7.

The internals view of the exemplary device charged by a USB charger is shown in FIG. 8. The device includes a charger base 827 (an exemplary USB charger) comprising a rare earth magnet charge base interface 824. The battery 803 (e.g., a Li-ion battery) is charged with the help of a flex PCB 804 continues down to make contact with battery terminal Also shown for the device are button 802, accelerometer 816, aerogel 814 and thermistor 815 to monitor and precisely control vaporization temperature. The mouthpiece is attached to the body from points 844 and 845. Various embodiments of mouthpiece as described herein or known to one of ordinary skilled in the art may be used.

Any material that is capable of being aerosolized and inhaled by a user may be incorporated into a device or cartridge of the devices described herein, as would be obvious to one skilled in the art. It is of particular interest that the material provides an experience to the user either in terms of tactile response in the respiratory tract, or in terms of visual feedback regarding the exhalation of the inhaled material. For example, many materials have be contemplated for use with the present invention including, but not limited to, those containing tobacco, natural or artificial flavorants, coffee grounds or coffee beans, mint, chamomile, lemon, honey, tea leaves, cocoa, and other non-tobacco alternatives based on other botanicals. A device or cartridge can also be compatible for use with pharmaceutical compounds or synthetic compounds, either for pharmaceutical or pleasurable use. Any such compound which can be vaporized (or volatized) at a relatively low temperature and without harmful degradation products can be suitable for use with a cartridge or device. Examples of compounds include, but are not limited to, menthol, caffeine, taurine, and nicotine.

Active elements contained in botanicals vaporize at different temperatures. The device can be calibrated to establish a single stable temperature, intended for vaporizing specific products, for example. A controller can also be used to select a variety of temperature settings. The user would choose which setting based on the type of cartridge used. The controller can also affect a desired temperature mechanically, such as by changing flow rate of the valve, or electronically, such as by electromechanical valve and microcontroller intermediary. For example, to change the operating temperature of a device, the oven chamber can be moved in respect to the temperature regulator, such as bimetallic discs.

Here, tobacco or tobacco material is defined as any combination of natural and synthetic material that can be vaporized for pleasure or medicinal use. In one embodiment, a cartridge can be prepared using cured tobacco, glycerin, and flavorings. Those skilled in the art of tobacco product manufacture are familiar with these and other ingredients used for cigarettes, cigars, and the like. The cartridge can be produced by chopping tobacco into fine pieces (for example, less than 2 mm diameter, preferably less than 1 mm), adding the other ingredients, and mixing until even consistency was achieved. In another embodiment, a cartridge can be prepared by processing the fill material into an even paste-like consistency (for example, particle size less than 1 mm), which facilitates the processing of filling the cartridge, for example, by use of an auger filler, peristaltic pump or a piston pump.

Preferably the material for use with a device as described herein or contained within a cartridge as described herein comprises at least one of a vapor-forming medium and a medium for providing a tactile response in a respiratory tract of a user. The aerosolized product from the material inserted into a device can be a combination of vapor phase gases as well as small droplets which have condensed out of vapor phase and remain suspended in the gas/air mixture (the latter constitutes the visible portion of the inhaled substance).

Propylene glycol (PG), glycerin, or a combination of both can be used as vapor-forming medium. Other vapor-forming media can be used with a cartridge and device as described herein. The vapor-forming medium serves to produce a visual vapor, such as a smoke-like vapor, when heated. This vapor can be visualized both before inhalation and during exhalation of the medium. PG has some advantages as compared to glycerin alone, as it exhibits a much higher vapor pressure at equivalent temperature and allows the device to operate at a lower temperature. Reducing the operating temperature conserves energy, and potentially can further improve the health benefits of using this system.

The user is prevented from touching the hot internal elements by surrounding insulating features. An exemplary device can include insulation for keeping the user from contacting the necessarily hot portion of the device. While greater thermal insulating ability is preferable so that the device performs with the best efficiency possible, an important aspect for the user is to perceive a relatively cool surface temperature. Various strategies can be employed to address the perception of the user regarding the temperature of the device. The device may be wrapped in a thermal insulating material that has enough durability for external use. Materials for this purpose have low thermal conductivity and low thermal capacity (specific heat). The combination of these properties can allow little heat to be transferred to the fingers of the user. Examples of materials with low thermal conductivity and capacity include some polymers and ceramics. A separate strategy is to use standoff features that keep the user from touching the higher temperature area directly. This can also minimize the contact area of the user's fingers and the device to additionally reduce perceived heat. The thermal conductivity and specific heat of the standoff features should be as low as possible.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for generating an inhalable aerosol, the device comprising:
   a body;
   an electronic heater disposed within the body, the electronic heater configured to heat a vaporizable material to generate the inhalable aerosol; and
   a controller, the controller configured to regulate an operating temperature of the electronic heater;
   wherein the electronic heater is further configured to operate in each of an on mode and a standby mode; and
   wherein the controller is further configured to:
      cause the electronic heater to convert from the standby mode to the on mode based on determining, while the electronic heater is in the standby mode, one or more of (i) movement of the device, (ii) removal of the device from a charging cradle, (iii) user touch of the device, (iv) that a user is puffing on the device, or (v) press of a touch-sensitive user interface; and
      cause the electronic heater to convert from the on mode to the standby mode based at least on determining, while the electronic heater is in the on mode, that the device has been placed in the charging cradle.

2. The device of claim 1, wherein a standby operating temperature of the electronic heater in the standby mode is 5° C. to 30° C. less than a set point operating temperature of the electronic heater in the on mode.

3. The device of claim 2, wherein the set point operating temperature is 165° C.

4. The device of claim 2, wherein the set point operating temperature of the electronic heater is fixed.

5. The device of claim 2, further comprising a user interface in communication with the controller;
   wherein the set point operating temperature of the electronic heater is a user-selectable operating temperature, the controller further configured to:
      receive, via the user interface, a user selection of the user-selectable operating temperature; and
      based on the receiving of the user selection, cause the electronic heater to maintain the user-selectable operating temperature while in the on mode.

6. The device of claim 1, wherein the controller is further configured to cause the electronic heater to convert from the on mode to the standby mode based on determining, while the electronic heater is in the on mode, one or more of (i) the electronic heater has been in the on mode for a predetermined length of time, (ii) a lack of movement of the device, or (iii) the device is in a specified position.

7. The device of claim 1, further comprising at least one sensor configured to detect movement of the device, the at least one sensor in communication with the controller and comprising at least one of an accelerometer, a tactile sensor, a vibration sensor, or a capacitive touch sensor;
wherein the controller is configured to determine the movement of the device based on the at least one sensor.

8. The device of claim 1, further comprising a thermistor in communication with the controller;
wherein the controller is further configured to determine that the user is puffing on the device based on monitoring of the thermistor.

9. The device of claim 1, wherein the electronic heater is further configured for an off mode; and
wherein the controller is further configured to cause the electronic heater to convert from the off mode to the on mode based on determining, while the electronic heater is in the off mode, one or more of (i) press of the touch-sensitive user interface, (ii) removal of the device from the charging cradle, or (iii) movement of the device.

10. The device of claim 1, wherein the electronic heater is further configured for an off mode; and
wherein the controller is further configured to:
disable motion-based activation of the electronic heater when the electronic heater is in the off mode; and
cause the electronic heater to convert from the off mode to the on mode based on determining, while the electronic heater is in the off mode, one or more of (i) press of the touch-sensitive user interface, or (ii) removal of the device from the charging cradle.

11. The device of claim 1, wherein the controller comprises a proportional integral derivative (PID) control loop, the PID control loop configured to control the electronic heater to maintain a set point operating temperature for the on mode and to maintain a standby operating temperature for the standby mode.

12. The device of claim 11, wherein the PID control loop comprises a thermistor located one of on or adjacent to a heater circuit of the electronic heater.

13. The device of claim 12, further comprising a microcontroller in communication with the thermistor;
wherein the microcontroller is configured to:
acquire A/D measurements; and
based on the A/D measurements, calculate a value for a PID control variable.

14. The device of claim 13, wherein the controller is further configured to, based at least on the PID control variable, affect one or more of a duty cycle or a power output of the heater circuit for the regulating of the operating temperature of the electronic heater.

* * * * *